US009521480B2

(12) United States Patent
Bauman et al.

(10) Patent No.: US 9,521,480 B2
(45) Date of Patent: Dec. 13, 2016

(54) VARIABLE NOISE ATTENUATOR WITH ADJUSTABLE ATTENUATION

(71) Applicants: Natan Bauman, Hamden, CT (US); Ralph T. Campagna, Danielson, CT (US)

(72) Inventors: Natan Bauman, Hamden, CT (US); Ralph T. Campagna, Danielson, CT (US)

( * ) Notice: Subject to any disclaimer, the term of this patent is extended or adjusted under 35 U.S.C. 154(b) by 44 days.

(21) Appl. No.: 14/448,732

(22) Filed: Jul. 31, 2014

(65) Prior Publication Data

US 2015/0036834 A1    Feb. 5, 2015

Related U.S. Application Data

(60) Provisional application No. 61/860,534, filed on Jul. 31, 2013.

(51) Int. Cl.
*A61F 11/06* (2006.01)
*H04R 1/10* (2006.01)
*H04R 5/033* (2006.01)
*H04R 25/00* (2006.01)

(52) U.S. Cl.
CPC .......... *H04R 1/1083* (2013.01); *H04R 1/1041* (2013.01); *H04R 5/033* (2013.01); *H04R 25/43* (2013.01); *H04R 2410/05* (2013.01); *H04R 2460/15* (2013.01)

(58) Field of Classification Search
CPC .................... A61F 2011/145; H04R 1/1083
USPC ........................................................ 381/72
See application file for complete search history.

(56) References Cited

U.S. PATENT DOCUMENTS

| 2,850,012 A | 9/1958 | Becker |
| 2,876,767 A | 3/1959 | Wasserman |
| 3,110,356 A | 11/1963 | Mendelson |
| 3,505,999 A | 4/1970 | Harvey et al. |
| 3,602,654 A | 8/1971 | Victoreen |
| 4,006,796 A | 2/1977 | Coehorst |
| 4,029,083 A | 6/1977 | Baylor |

(Continued)

FOREIGN PATENT DOCUMENTS

| EP | 0077688 A1 | 4/1983 |
| EP | 1326479 B1 | 7/2003 |

OTHER PUBLICATIONS

Schmid, Aging Nation Faces Growing Hearing Loss, Copyright 2007—Assosiated Press.

(Continued)

*Primary Examiner* — Simon King
(74) *Attorney, Agent, or Firm* — St Onge Steward Johnston and Reens LLC (57) ABSTRACT

An ear attenuator headset that allows a user to adjust the amount of attenuation in a variable, continuous fashion from zero attenuation to maximum attenuation without removing the device from a user's head. The ear attenuator headset includes a passageway, the passageway allowing for sound to pass through the headset and a control element, the control element able to control the amount of sound that passes through the passageway of the ear attenuator headset. The ear attenuator can be used in headsets, headphones, and earbuds where electronic sounds are transmitted and added variable attenuation is also available for the consumer to take advantage of for reduction of the external environmental sounds.

24 Claims, 6 Drawing Sheets

(56) References Cited

U.S. PATENT DOCUMENTS

| | | | |
|---|---|---|---|
| 4,060,080 A | 11/1977 | Akiyama | |
| 4,232,084 A | 11/1980 | Tate | |
| 4,556,122 A | 12/1985 | Goode | |
| 4,834,211 A | 5/1989 | Bibby et al. | |
| 4,896,679 A | 1/1990 | St. Pierre | |
| 4,913,165 A | 4/1990 | Fishgoyt | |
| 5,131,411 A | 7/1992 | Casali et al. | |
| 5,333,622 A | 8/1994 | Casali et al. | |
| 5,600,729 A | 2/1997 | Darlington et al. | |
| 5,651,071 A | 7/1997 | Lindemann et al. | |
| 5,675,658 A | 10/1997 | Brittain | |
| 6,082,485 A | 7/2000 | Smith | |
| 6,286,622 B1 * | 9/2001 | Tiemann | A61F 11/08 128/864 |
| 6,368,288 B2 | 4/2002 | Stone | |
| 6,368,289 B2 | 4/2002 | Stone | |
| 6,440,102 B1 | 8/2002 | Arenberg et al. | |
| 7,171,371 B2 | 1/2007 | Goldstein | |
| 7,424,123 B2 | 9/2008 | Shennib et al. | |
| 7,756,281 B2 | 7/2010 | Goldstein et al. | |
| 7,779,844 B2 | 8/2010 | Purcell et al. | |
| 7,817,803 B2 | 10/2010 | Goldstein | |
| 7,822,219 B2 | 10/2010 | Baker et al. | |
| 7,837,008 B1 | 11/2010 | Lane et al. | |
| 7,882,928 B2 | 2/2011 | McMahon et al. | |
| 7,886,745 B2 | 2/2011 | Purcell et al. | |
| 7,913,696 B2 | 3/2011 | Purcell et al. | |
| 8,018,328 B2 | 9/2011 | Goldstein et al. | |
| 8,047,207 B2 | 11/2011 | Perez et al. | |
| 8,081,780 B2 | 12/2011 | Goldstein et al. | |
| 8,111,839 B2 | 2/2012 | Goldstein et al. | |
| 8,118,031 B2 | 2/2012 | Seville | |
| 8,142,870 B2 | 3/2012 | Keady | |
| 8,150,043 B2 | 4/2012 | Goldstein et al. | |
| 8,150,044 B2 | 4/2012 | Goldstein et al. | |
| 8,155,361 B2 | 4/2012 | Schindler | |
| 8,170,228 B2 | 5/2012 | Goldstein et al. | |
| 8,194,864 B2 | 6/2012 | Goldstein et al. | |
| 8,194,865 B2 | 6/2012 | Goldstein et al. | |
| 8,199,919 B2 | 6/2012 | Goldstein et al. | |
| 8,208,644 B2 | 6/2012 | Goldstein et al. | |
| 8,208,652 B2 | 6/2012 | Keady | |
| 8,213,629 B2 | 7/2012 | Goldstein et al. | |
| 8,213,649 B2 | 7/2012 | Goldstein et al. | |
| 8,221,860 B2 | 7/2012 | Keady | |
| 8,221,861 B2 | 7/2012 | Keady | |
| 8,229,128 B2 | 7/2012 | Keady | |
| 8,251,925 B2 | 8/2012 | Keady et al. | |
| 8,311,228 B2 | 11/2012 | Goldstein et al. | |
| 8,312,960 B2 | 11/2012 | Keady | |
| 8,315,400 B2 | 11/2012 | Goldstein et al. | |
| 8,319,620 B2 | 11/2012 | Usher et al. | |
| 8,326,628 B2 | 12/2012 | Goldstein et al. | |
| 8,326,635 B2 | 12/2012 | Usher et al. | |
| 8,340,333 B2 | 12/2012 | Wilson | |
| 8,437,492 B2 | 5/2013 | Goldstein et al. | |
| 8,447,031 B2 | 5/2013 | Usher et al. | |
| 8,550,206 B2 | 10/2013 | Keady et al. | |
| 8,820,470 B2 | 9/2014 | Brown | |
| 2002/0143242 A1 | 10/2002 | Nemirovski | |
| 2002/0146142 A1 * | 10/2002 | Myers | A61F 11/14 381/371 |
| 2006/0042868 A1 | 3/2006 | Berg et al. | |
| 2007/0270988 A1 | 11/2007 | Goldstein et al. | |
| 2008/0015463 A1 | 1/2008 | Goldstein | |
| 2008/0031475 A1 | 2/2008 | Goldstein | |
| 2008/0037797 A1 | 2/2008 | Goldstein et al. | |
| 2008/0046246 A1 | 2/2008 | Goldstein et al. | |
| 2008/0130906 A1 | 6/2008 | Goldstein et al. | |
| 2008/0137873 A1 | 6/2008 | Goldstein | |
| 2008/0144840 A1 | 6/2008 | Goldstein et al. | |
| 2008/0144841 A1 | 6/2008 | Goldstein et al. | |
| 2008/0144842 A1 | 6/2008 | Goldstein et al. | |
| 2008/0176289 A1 | 7/2008 | Zeng et al. | |
| 2008/0178088 A1 | 7/2008 | Goldstein et al. | |
| 2008/0181419 A1 | 7/2008 | Goldstein et al. | |
| 2008/0181442 A1 | 7/2008 | Goldstein et al. | |
| 2008/0205660 A1 | 8/2008 | Goldstein | |
| 2008/0212787 A1 | 9/2008 | Goldstein et al. | |
| 2008/0219456 A1 | 9/2008 | Goldstein et al. | |
| 2008/0219486 A1 | 9/2008 | Goldstein et al. | |
| 2008/0240458 A1 | 10/2008 | Goldstein et al. | |
| 2008/0253583 A1 | 10/2008 | Goldstein et al. | |
| 2008/0267416 A1 | 10/2008 | Goldstein et al. | |
| 2008/0269636 A1 | 10/2008 | Burrows et al. | |
| 2008/0299339 A1 | 12/2008 | Keady | |
| 2008/0311324 A1 | 12/2008 | Keady | |
| 2009/0016541 A1 | 1/2009 | Goldstein et al. | |
| 2009/0016542 A1 | 1/2009 | Goldstein et al. | |
| 2009/0022294 A1 | 1/2009 | Goldstein et al. | |
| 2009/0022353 A1 | 1/2009 | Goldstein et al. | |
| 2009/0028356 A1 | 1/2009 | Ambrose et al. | |
| 2009/0034748 A1 | 2/2009 | Sibbald | |
| 2009/0034765 A1 | 2/2009 | Boillot et al. | |
| 2009/0067661 A1 | 3/2009 | Keady et al. | |
| 2009/0071486 A1 | 3/2009 | Perez et al. | |
| 2009/0071487 A1 | 3/2009 | Keady | |
| 2009/0130423 A1 | 5/2009 | Keady | |
| 2009/0146799 A1 | 6/2009 | Goldstein et al. | |
| 2009/0147966 A1 | 6/2009 | McIntosh et al. | |
| 2009/0154748 A1 | 6/2009 | Baker et al. | |
| 2009/0155518 A1 | 6/2009 | Keady | |
| 2009/0192407 A1 | 7/2009 | Keady et al. | |
| 2009/0214072 A1 | 8/2009 | Staab et al. | |
| 2009/0220096 A1 | 9/2009 | Usher et al. | |
| 2009/0238374 A1 | 9/2009 | Keady | |
| 2009/0238386 A1 | 9/2009 | Usher et al. | |
| 2009/0240497 A1 | 9/2009 | Usher et al. | |
| 2009/0245530 A1 | 10/2009 | Keady | |
| 2009/0264161 A1 | 10/2009 | Usher et al. | |
| 2009/0290721 A1 | 11/2009 | Goldstein et al. | |
| 2010/0002897 A1 | 1/2010 | Keady | |
| 2010/0012420 A1 | 1/2010 | Keady | |
| 2010/0033313 A1 | 2/2010 | Keady et al. | |
| 2010/0071707 A1 | 3/2010 | Wohl | |
| 2010/0074451 A1 | 3/2010 | Usher et al. | |
| 2010/0076793 A1 | 3/2010 | Goldstein et al. | |
| 2010/0135502 A1 | 6/2010 | Keady et al. | |
| 2010/0142715 A1 | 6/2010 | Goldstein et al. | |
| 2010/0142725 A1 | 6/2010 | Goldstein et al. | |
| 2010/0177918 A1 | 7/2010 | Keady et al. | |
| 2010/0241256 A1 | 9/2010 | Goldstein et al. | |
| 2010/0322454 A1 | 12/2010 | Ambrose et al. | |
| 2011/0079227 A1 | 4/2011 | Turcot et al. | |
| 2011/0085689 A1 | 4/2011 | Keady | |
| 2011/0115626 A1 | 5/2011 | Goldstein et al. | |
| 2011/0158420 A1 | 6/2011 | Hannah | |
| 2011/0206214 A1 | 8/2011 | Christoph et al. | |
| 2011/0228963 A1 | 9/2011 | Goldstein et al. | |
| 2011/0235843 A1 | 9/2011 | Keady et al. | |
| 2011/0311079 A1 | 12/2011 | Keady | |
| 2012/0101514 A1 | 4/2012 | Keady et al. | |
| 2012/0103346 A1 | 5/2012 | Keady | |
| 2012/0123573 A1 | 5/2012 | Goldstein et al. | |
| 2012/0177209 A1 | 7/2012 | Goldstein et al. | |
| 2012/0177210 A1 | 7/2012 | Goldstein et al. | |
| 2012/0207320 A1 * | 8/2012 | Avital | H04R 1/1041 381/74 |
| 2012/0288104 A1 | 11/2012 | Goldstein et al. | |
| 2012/0318605 A1 | 12/2012 | Brown | |
| 2013/0035608 A1 | 2/2013 | Goldstein et al. | |
| 2013/0039518 A1 | 2/2013 | Goldstein et al. | |
| 2013/0098706 A1 | 4/2013 | Keady | |
| 2013/0123919 A1 | 5/2013 | Goldstein et al. | |
| 2014/0270257 A1 | 9/2014 | Bauman et al. | |

OTHER PUBLICATIONS

International Search Report and Written Opinion of the International Searching Authority Application No. PCT/US2014/030252 Completed: Jul. 10, 2014; Mailing Date: Aug. 1, 2014 9 pages.
Passchier-Vermeer, et al., "Noise Exposure and Public Health", Environ Health Persoect., Mar. 2000, pp. 123-131 (abstract only).

(56) References Cited

OTHER PUBLICATIONS

Rosenhall, et al., "Presbycusis and Noise-Induced Hearing Loss"; Ear Hear, Aug. 1990, 1 page abstract.

* cited by examiner

VARIABLE NOISE ATTENUATOR WITH ADJUSTABLE ATTENUATION

FIELD OF THE INVENTION

A variable ear attenuator and headset that allows a user to adjust the amount of attenuation in a variable, continuous fashion from zero attenuation to maximum attenuation without removing the attenuator from a user's ear or the headset from a user's head

BACKGROUND OF THE INVENTION

According to Occupational Safety & Health Administration (OSHA), about 30 million people in the United States are exposed to hazardous occupational noise every year. Noise-related hearing loss has been listed as one of the most widespread occupational health concerns in the United States for more than 25 years. Thousands of workers every year suffer from preventable hearing loss due to high workplace noise levels.

A problem exists whereby there is a need to provide an ear attenuator or an ear attenuator headset which allows a user to change the amount of sound protection quickly and according to the amount of noise in the environment, while also being able to allow for communication between the user and another person. For example, at a construction site, at one moment a construction worker needs to be protected from very loud construction equipment and at a moment later the same construction worker needs to be able to recognize warning sounds or instructions given by a supervisor.

In another example, a hunter needs to hear the faint sounds of animal being hunted, but yet at the time of rifle fire the hunter needs to protect his or her hearing. On a battle field soldiers need to protect their hearing from very loud explosions, but also they also need to hear comments as well as very faint sounds and instructions from their officers. Furthermore, a musician who wants to protect his hearing may also need to hear instructions given by a conductor.

Therefore, it is desirable to provide an ear attenuator and/or an ear attenuator headset that has a variable control that allows a user to quickly adjust the amount of sound protection according to the amount of noise in the environment, while also being able to maintain communication between the user and a person giving instructions or commands to the user. Such uses include headsets for daily use and/or headsets, as well as earbuds for listening to electronically fed sounds for personal use.

It is desirable to have an ear attenuator and/or ear attenuator headset that provides, for example music or speech to be played, while allowing for a variable, continuous changing attenuation selected by the user, according to the environment's noise level, instead of a device with a noise cancelling system which deprives the user from hearing environmental sounds such as warning sounds of incoming traffic.

There is evidence that auditory deprivation can result in increase of hearing sensitivity which in turn has been shown to increase incidence of tinnitus, hyperacusis and other sound sensitivity disorders. Therefore, sound cancelling devices can present a risk of provoking any and all of those auditory symptoms. A variable attenuator such as one proposed in this invention will provide needed sound protection on one hand and at the same time provide prevention for developing above mentioned auditory disorders.

In addition, according to a 2007 review of noise cancelling devices (as reported by the New York Times) the sound quality of the music may be not as good as it is without non-cancelling high quality headphones. Also, this report claims that the active (electronic) cancelling headphones emit a low hissing sound when music is not played. All such problems are non-existent in a passive sound protective device such as proposed in this invention.

SUMMARY OF THE INVENTION

Accordingly, it is an object of the invention to allow for changing the level of attenuation for those who are in need of ear protection. It is another object of the invention to provide a device that allows the level of attenuation to be changed, so as not to impede communication. It is another object of the invention to provide a device where the user can adjust the amount of attenuation in a variable, continuous fashion from zero attenuation to maximum attenuation without removing the device from the ear or head of the user in all listening devices such as headphones, headsets, earbuds etc.

These objects of the invention are achieved by providing an ear attenuator headset comprising: at least one earcup, the at least one earcup having a passageway through the at least one earcup allowing for sound to pass through; and a control element, the control element able to control the amount of sound that passes through the at least one earcup.

In certain embodiments, the ear attenuator headset includes a headstrap, the head strap connecting a first earcup to a second earcup.

In certain embodiments, the control element includes a blocking member, the blocking member able to control the amount of sound that passes through the passageway of the at least one earcup. In certain embodiments, the control of the amount of sound that passes through the passageway is a physical control, such that the blocking member blocks sound waves from passing through the passageway. In certain embodiments, the blocking member partially blocks the passageway, requiring the sound and sound waves to have to pass around the blocking member in order to reach a user's ear. In certain embodiments, the blocking member is able to adjust the width of the passageway through the at least one earcup.

In certain embodiments, the control element includes a knob that is connected to the blocking member. In certain embodiments, the knob is ribbed and/or has a position indicator indicating how much attenuation the knob is giving at any given time. In certain embodiments the knob is located on the earcup. In certain embodiments, the knob is located on the outer surface of the earcup such that it extends outwardly from the earcup.

In other embodiments, the control element is an electronic control that is accessed via a touchscreen. In certain embodiments, the control element can be manipulated via touch technology.

In certain embodiments, the blocking member is made of foam attenuating material and/or rubber and/or any other sound blocking material. In certain embodiments, the blocking member is an insulator that prohibits the passage of sound and sound waves through the blocking member.

In certain embodiments, the blocking member is able to rotate to control the amount of sound that passes through the passageway. In certain embodiments, the blocking member is able to move axially (or parallel to the length of the passageway). In certain embodiments, the blocking member is able to move in a screw-like or helical manner. In certain embodiments, the blocking member is larger than the width of the passageway. In certain embodiments, the blocking member does not rotate to control the amount of sound that passes through the passageway.

In certain embodiments, when the knob is in the closed position the blocking member is aligned with the passageway in the at least one earcup, and when the knob is in the open position, the blocking member is not aligned with the passageway in the at least one earcup. In certain embodiments, when the knob is in the open position, there is a space between the blocking member and the passageway, so that sound is able to pass around the blocking member and through the passageway.

In certain embodiments, the blocking member is connected to the knob via a screw or other fastening device. In certain embodiments, when the knob is rotated, the screw tightens and the blocking member is brought closer to the knob to cover a portion of the passageway. This blocks the sounds and prevents sound from passing through the passageway.

In certain embodiments, the at least one earcup includes a plate and wherein when the knob is rotated to a closed position, the blocking member engages the plate. In certain embodiments, when the blocking member engages the plate, little to no sound can pass through the passageway, thus providing for complete attenuation. In certain embodiments, when the blocking member engages the plate, the ends of the blocking member engage the plate, while the central portion of the blocking member blocks the passageway.

In certain embodiments, sound passes through the passageway in the portion of the passageway between the plate and the blocking member. This occurs when the knob is not in a fully closed position, but rather in a partially closed position. In certain embodiments, the plate is a disc. In certain embodiments, the disc has a circular or oval shape. In certain embodiments, the disc has a shape that corresponds to the shape of the passageway between the plate and the blocking member.

In another embodiment of the invention, the blocking member is fixed to a knob and the knob is slidable along the at least one earcup. In this embodiment, the at least one earcup includes a bore, the knob being slidable within the bore. In certain embodiments, the bore has a substantially rectangular shape. In certain embodiments, the knob has a greater width than the bore. In certain embodiments, the knob is connected to a blocking member by a screw that has a width that is slightly less than the width of the bore. In certain embodiments, the bore includes a track whereby the knob is slidable within the track.

In certain embodiments, when the knob is in the closed position the blocking member is aligned with the passageway in the at least one earcup, and when the knob is in the open position, the blocking member is not aligned with the passageway in the at least one earcup.

In certain embodiments, the at least one earcup includes a plate and wherein when the knob is slid to a closed position, the blocking member is aligned with the passageway in the at least one earcup and closes the passageway in the at least one earcup.

In certain embodiments, the blocking member partially blocks the passageway in the at least one earcup, thus providing for partial attenuation through the at least one earcup. In this embodiment, the sound passes through the passageway, but is obstructed and the passage is not freely open to allow the passing of sound.

In certain embodiments, the blocking member is made of foam and/or rubber or any other pliable material or any insulating material. In certain embodiments, the blocking member is made of an insulator material that blocks sound from passing through the blocking member.

In certain embodiments, the control element is controlled by a remote control or other control device which closes or opens the passageway through the at least one earcup allowing for sound to pass through. In certain embodiments, the remote control can be located away from or remote from the at least one earcup. In other embodiments, the remote control may be attached to or linked to the at least one earcup via an electronic cable. In certain embodiments, the remote control or other control device is considered a secondary control. In certain embodiments, the secondary control is a computer or includes electronic elements such as a processor and software executing on the processor.

In certain embodiments, the remote control changes the size of the passageway (also the attenuation space (AS)) based upon the detected amount of sound in the environment. In certain embodiments, the width, length and/or depth of the passageway may be changed by the remote control. In certain embodiments, the ear attenuator headset includes a sensor or noise detector (such as a microphone) to detect the amount of external sound that is present in the environment. In certain embodiments, the sensor or noise detector controls the amount of attenuation of the ear attenuator headset. In certain embodiments, the sensor or noise detector automatically controls and/or changes the amount of attenuation of the ear attenuator headset based upon the amount of external sound that is present in the environment. In certain embodiments, software executing on a processer is in communication with the sensor or noise detector to control and/or changes the amount of attenuation of the ear attenuator.

In certain embodiments, the sensor or noise detector is located in the at least one earcup or in the strap. In certain embodiments, the sensor or noise detector is located in the remote control. In certain embodiments, the sensor or noise detector is located in the secondary control.

Other objects of the invention are achieved by providing an ear attenuator headset comprising: two earcups, each of the two earcups having a passageway through the two earcups allowing for sound to pass through; and a control element, the control element able to control the amount of sound that passes through the passageway, the control element having a blocking element that blocks the sound from passing through the passageway through the at least one earcup and allowing for variable control of the sound passing through the passageway.

In certain embodiments, the two earcups are each controlled by the same control element. In certain embodiments, a second control element is provided, whereby the first and second control element each controls a passageway in each one of the earcups. In certain embodiments, the first and second control elements are linked, so that if one control element is adjusted, the amount of attenuation in each one of the earcups is controlled.

Other objects of the invention are achieved by providing variable attenuation in earphones or headphones which deliver sound (for example music), but at the same time also need to provide attenuation, such as in an active ear attenuators (for example devices with noise cancelling systems).

Other objects of the invention include variable attenuators in sound monitoring devices which also require attenuation (example, musicians who require a live sound feed and protection from loud sound).

Yet, in another embodiment the variable attenuator is placed within a hearing aid system which may also require to vary the amount of environmental sound allowed to be heard by the hearing aid user. This can be accomplished by placing the core of the attenuator for example into an earmold attached to the hearing aid device.

Similarly, such described variable attenuator can be placed into a device used for tinnitus and or various sound sensitivity treatment devices which may also require a variable change in the amount of sound transmitted from the environment into the user's ear.

In these embodiments, variable attenuation devices are provided so that external sound can be controlled through the attenuation device.

Other objects of the invention are achieved by providing an ear attenuator headset comprising: at least one earcup, the at least one earcup having a passageway through the at least one earcup allowing for sound to pass through; a control element, the control element able to control the amount of sound that passes through the at least one earcup; and a plurality of attenuator discs, wherein as control element is turned, one of the plurality of discs is inserted into the passageway through the earcup to control the amount sound that passes through the at least one earcup.

In certain embodiments, the control element is a knob that is able to be turned. In certain embodiments, the plurality of discs are stored in a core of the at least one earcup. In certain embodiments, the core contains several discs.

In certain embodiments, as the control element is turned, a disc is inserted (or partially inserted) into the passageway through the earcup to control the amount sound that passes through the at least one earcup. In certain embodiments, as the control element continues to be turned, the disc in the passageway is replaced by a larger disc or a disk with a greater sound attenuation factor to increase the amount of attenuation of the at least one earcup and reduce the amount of sound through the passageway.

In certain embodiments, a greater or smaller attenuation disc is inserted into the at least one passageway as the control element is turned. In certain embodiments, attenuator discs of different sizes are inserted into the passageway, such that more than one attenuator discs can be inserted into the passageway.

In certain embodiments, as additional attenuator discs are inserted into the passageway, the discs form a cone shaped attenuator element. In certain embodiments, the cone shaped attenuator element is a series of flat discs, each disc having a pancake shape.

In certain embodiments, the control element and the attenuator discs are controlled remotely by a remote control or by radio frequency or any other form of wireless streaming. In certain embodiments, other remote means of control are used to control the amount of attenuation through the at least one earcup. In certain embodiments, Bluetooth or other wireless control methods may be used to control the amount of attenuation through the at least one earcup. In certain embodiments, a computer and/or a processor that sends electronic signals is used to control the amount of attenuation through the at least one earcup.

In certain embodiments, the plurality of discs can be replaced by an insert that can be used to change the attenuation factor through the passageway.

In certain embodiments, the at least one passageway is replaced by core, such that the plurality discs are stored in the core and the discs are removed from the core to increase the amount of sound that is able to pass through the core. In certain embodiments, the discs can be returned to the core to decrease the amount of sound that can pass through the core.

In certain embodiments, the discs are made of foam attenuating material and/or rubber.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention

BRIEF DESCRIPTION OF THE DRAWINGS

FIGS. 4A-2D schematically illustrate a cross-section view of the variable ear attenuator of FIG. 3 with the attenuator in various positions;

DETAILED DESCRIPTION OF THE INVENTION

This application incorporates by reference all subject matter included in U.S. Provisional Ser. No. 61/860,534 entitled "Variable Noise Attenuator with Adjustable Attenuation" filed Jul. 31, 2013.

This application incorporates by reference all subject matter included in U.S. Provisional Ser. No. 61/790,243 entitled "Variable Noise Attenuator" filed Mar. 15, 2013.

This application incorporates by reference all subject matter included in U.S. Ser. No. 14/212,409 entitled "Variable Sound Attenuator" filed Mar. 14, 2014.

Figure 1:
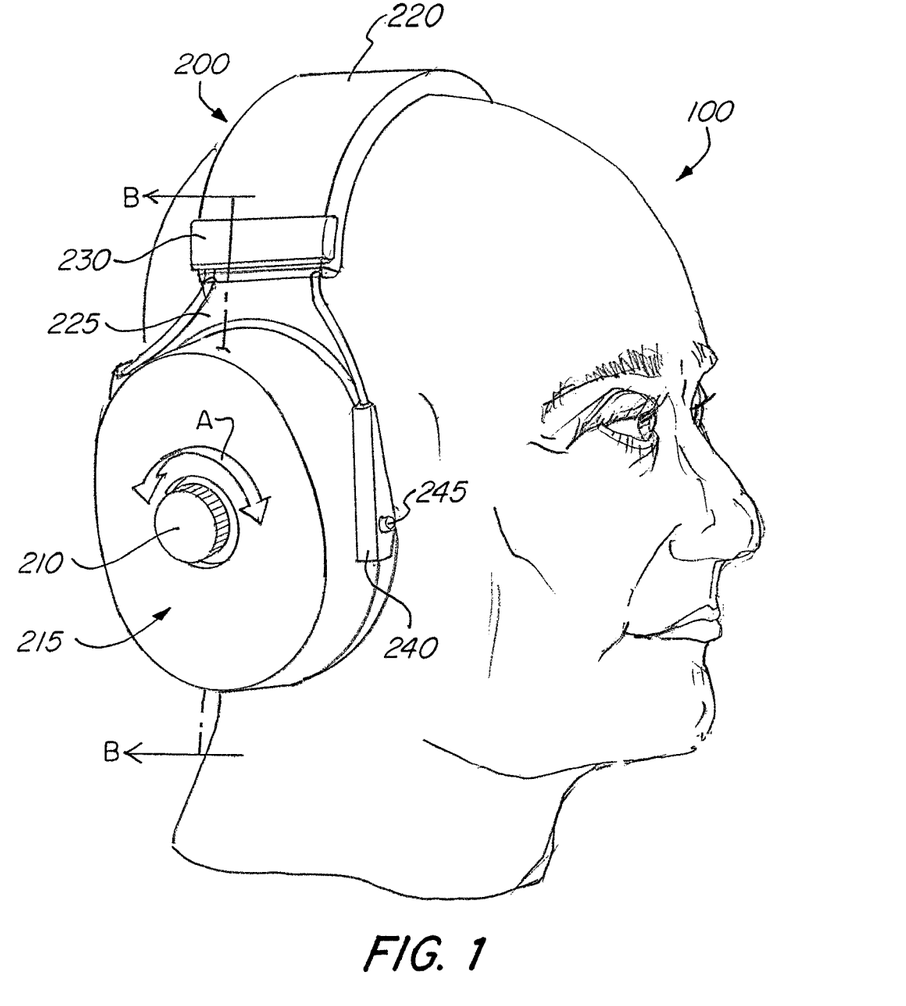
FIG. 1 schematically illustrates a perspective view of a headset having a variable ear attenuator with adjustable attenuation of one embodiment of the invention.

Referring to FIG. 1, an ear attenuator headset 200 is shown being placed on the head of a user 100. The variable attenuator headset 200 is shown having an earcup 215 being connected to a strap 220/225, which has adjustment member 230, that is able to adjust the size of strap 220/25, so that it comfortable fits the user's head.

In FIG. 1, control element 210 is shown as a knob whereby the knob can be rotated along arrow A. Power control 240 is shown having on switch 245, whereby the ear attenuator headset 200 can be turned on or off.

In certain embodiments, the control element 210 does not extend or extends just minimally past the earcup 215, such that the attenuator 200 appears to be an ordinary headset.

Figure 2A:
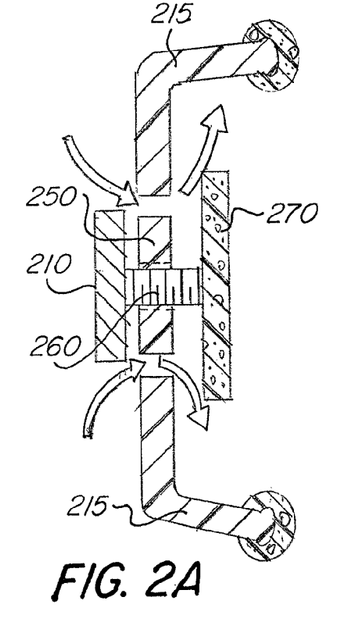
FIGS. 2A-2D schematically illustrate a cross-section view of the variable ear attenuator of FIG. 1 with the attenuator in various positions.
Figure 2B:
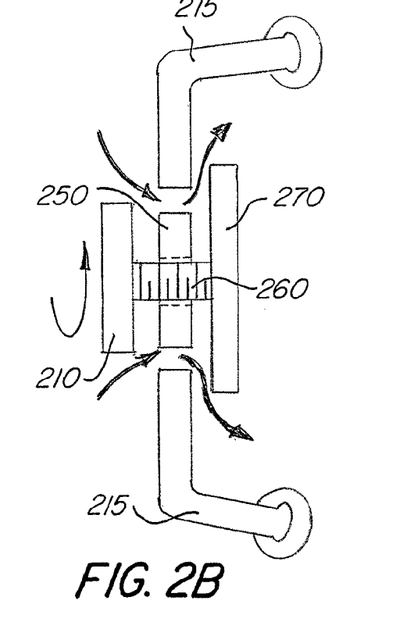
Figure 2C:
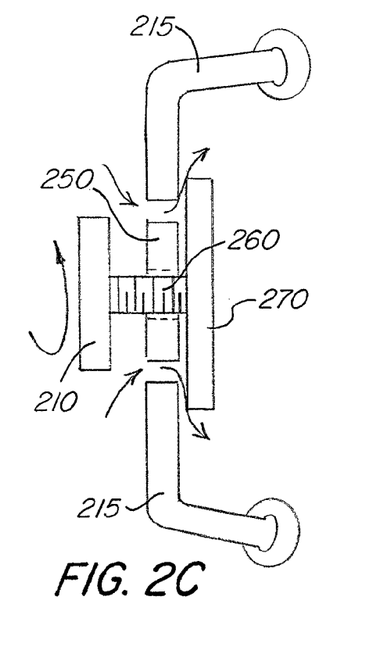
Figure 2D:
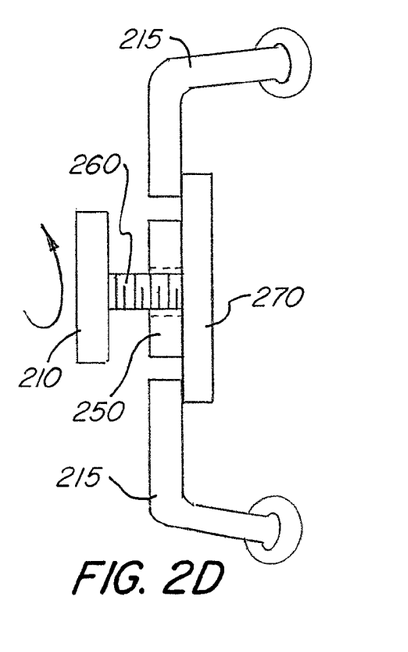

In FIGS. 2A-2D, various cross sections along axis B-B of ear attenuator headset 200 are shown. FIG. 2A shows the open position of ear attenuator headset 200. FIG. 2B shows a 60% open position, FIG. 2C shows a 30% open position and FIG. 2D shows a closed position. The control element 210 is rotated to control the amount of attenuation through the at least one earcup 215. The amount of attenuation can be modified as the control element 210 is rotated.

In the cross-section view of FIGS. 2A-2D, the control element 210 is connected via a fastening element 260 (shown as a screw) to a plate 250, which is then connected to a blocking member 210. The blocking member 210 can be made of foam or other attenuating material. The plate 250 is the outer portion of the earcup 215. The plate 250 may be flat or may have a curved shape according to a headset As control element 210 is turned, the blocking member 270 moves axially with respect to the control element 210, such that in FIG. 2A, the blocking member is furthest from the control element 210 (the open position) and in FIG. 2D the blocking member is closest to the control element 210 and is flush against the earcup 215, closing the passageway through the earcup 215.

In certain embodiments, the blocking member 270 rotates when the control element 210 is rotated. In other embodiments, the blocking member 270 does not rotate when the control element 210 is rotated, but rather moves in a straight line path when the control element 210 is rotated.

The attenuator works on the fact that the greater the opening in the passageway, the greater the amount of sound that can pass through the passageway, as the blocking member 270 prevents the passage of sound, thus providing attenuation.

As the control element 210 rotates, the amount of rotation of the control element 210 allows for varying levels of attenuation through the earcup 215. Shown are levels where the device is fully open, 60% open, 30% open and closed. As the control element 210 is turned to tighten the blocking member 270 towards the plate 250, the level of attenuation decreases as the blocking member is tightened. As the blocking member is tightened with respect to the control element 210, less sound is able to pass through the passageway.

In the fully open, 60% open, and 30% open diagrams, the sound is able to pass through the top portion of the passageway, around the blocking member 270 and through the rest of the passageway into a user's ear. However, in the closed position, the blocking member 270 prevents sound from passing through the passageway and the sound is reflected back and not able to be heard by a person wearing the device. When closed, the device provides for complete attenuation. When open, the device provides enough sound to enter the passageway to make voice audible. When partial attenuation is desired, the control element gives a varying degree of sound flow through.

Figure 3:
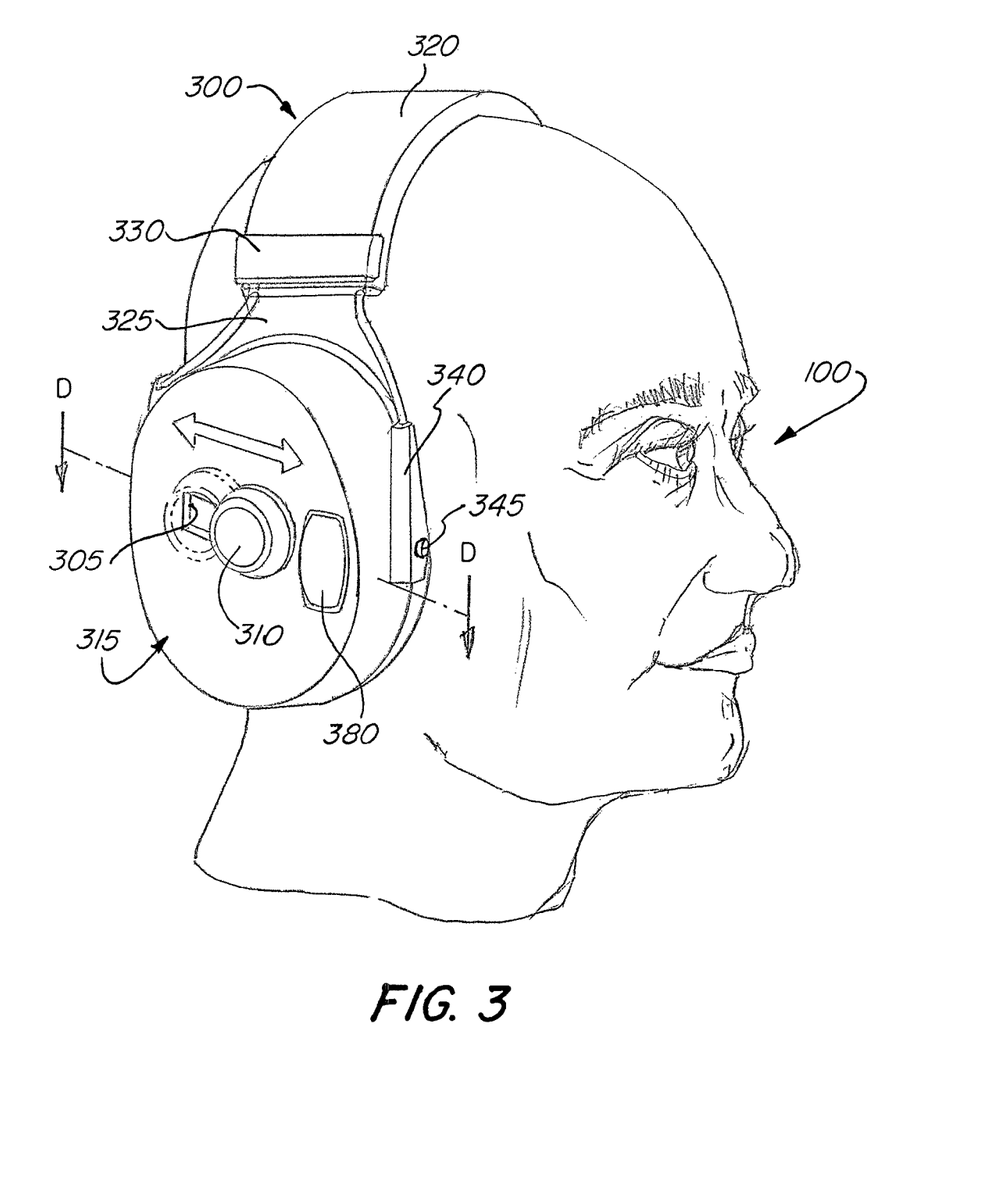
FIG. 3 schematically illustrates a perspective view of a headset having a variable ear attenuator with adjustable attenuation of another embodiment of the invention.

Referring to FIG. 3, another embodiment of the invention is shown. Here, the control element 310 (shown as a knob) is slidable with respect to a bore 305 in the ear attenuator headset 300. The ear attenuator headset 300 is shown located on the head of a person 100.

In FIG. 3, the control element 310 is shown having a greater width than the passageway (rectangular bore 305), and is able to slide along the outside of the ear attenuator 300 in a manner that is perpendicular to the passageway and along arrow C. The earcup 315 is shown being attached via a strap 320/235 with adjustable element 330.

As the knob 310 slides, it can go from a position where the blocking member does not cover the passageway (fully open) to a position where the blocking member covers the passageway (closed) and prevents sound from passing through the passageway.

In certain embodiments, the control element 310 does not extend or extends just minimally past the earcup 315, such that the attenuator 300 appears to be an ordinary headset.

In certain embodiments, the ear attenuator headset 300 is shown having an audio source 380. The audio source 380 provides a sound to a user and is reminiscent of the audio source on a standard headset. The audio source can receive sounds from a wire or from a wireless source, such that the ear attenuator headset 300 can either be powered via batteries (in a wireless version) or can draw power from a device that it is plugged into via a wire. The audio source can be controlled via Bluetooth and can include a processor whereby software executes on the processor to control the audio source. The audio source 380 can also be provided in various additional embodiments of the invention, for example, in the embodiments shown in FIGS. 1, 2A-2D, and 5-7.

As shown in FIGS. 4A-4D, various positions of the attenuator are shown along axis D-D of the device.

Figure 4A:
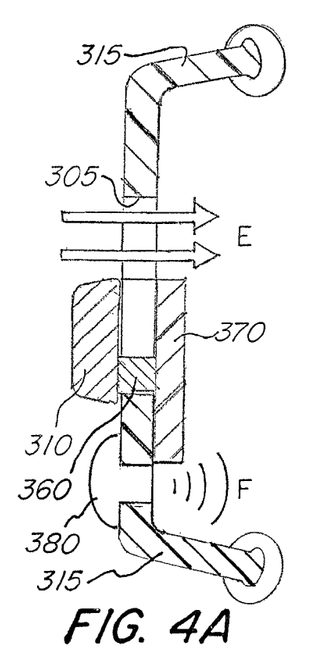

FIG. 4A shows the attenuator 300 in an open position having passageway E, whereby sound is able to pass through the earcup 315 into a person's ear.

Also shown in FIG. 4A is control element 310, which is held via a screw 360 to a blocking member 370. The blocking member 270 prevents the passage of sound, thus providing attenuation. The blocking member 270 can be made of foam or other attenuating material, such as foam and/or rubber than prevents sound from passing through the blocking material.

Also shown in FIG. 4A is the audio source 380 with acoustic signal F. The acoustic signal F is sound that comes from an audio source on a standard headset.

Having both the audio source 380 allows a user to listen to music. If another person asks the user a question, the user can hear the person without having to remove the ear attenuator device 300 from the user's head, as external noise can pass through the passageway.

Figure 4B:
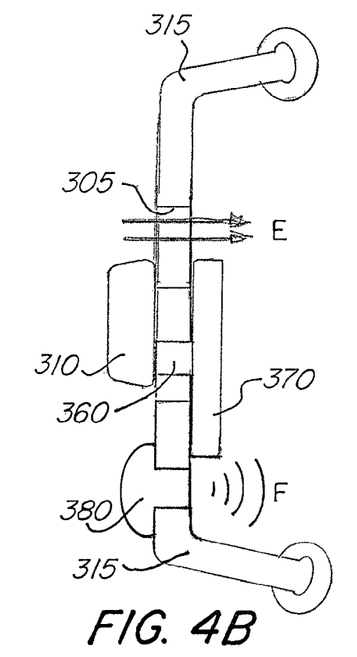
Figure 4C:
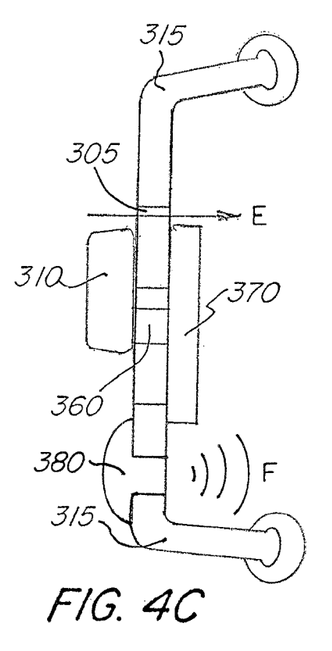
Figure 4D:
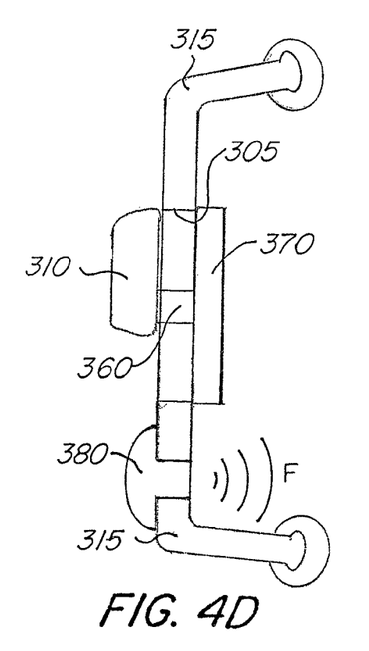

FIG. 4A shows the open position, FIG. 4B shows a position whereby the attenuator is 60% open, FIG. 4C shows a position that is 30% open and FIG. 4D shows the closed position. In certain embodiments, the position of the knob can be varied, which allows a user to control the level of attenuation of the device.

The blocking member 270 is able to slide to block the passageway to control the level of attenuation in the device. In certain embodiments, as the blocking member 270 slides, it tightens with respect to the earcup 315 and forms an airtight seal to provide complete attenuation in the closed position.

In certain embodiments, a screen is provided such that the screen prevents debris from entering the device. The screen does not prevent sound from entering the passageway.

Figure 5:
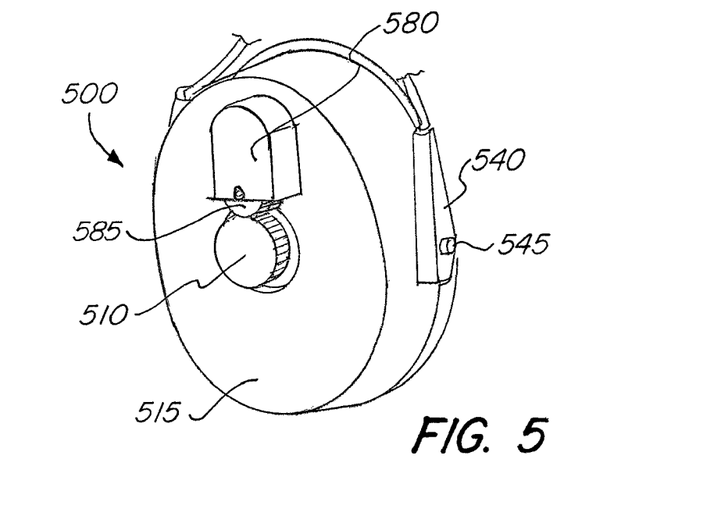
FIG. 5 schematically illustrates a perspective view of a headset having a variable ear attenuator with adjustable attenuation of another embodiment of the invention.

FIG. 5 shows another embodiment of the invention whereby an external power source is used to power the control element. In FIG. 5, attenuator device 500 includes an earcup 515 and a control element 510, the control element 510 able to control the blocking element in the same manner as shown in FIG. 1 and as described in FIGS. 2A-2D.

Additionally, FIG. 5 shows power source 580, the power source 580 being controlled by an external element such as Bluetooth or by a controller.

The power source 580 is able to control the rotation of control element 510, to control attenuation of the device. In certain instances, this is useful as a user may not be able to physically control the control element 510, as in the case of a user lacking coordination or even lacking the ability to perform such a maneuver as a result of an injury.

In certain embodiments, the earcup 515 includes a processor and software executing on the processor, such that the software is able to control the power source 580. In certain embodiments, a computer or non-transient medium is used to store instructions to control the power source 580 and the control element.

Figure 6:
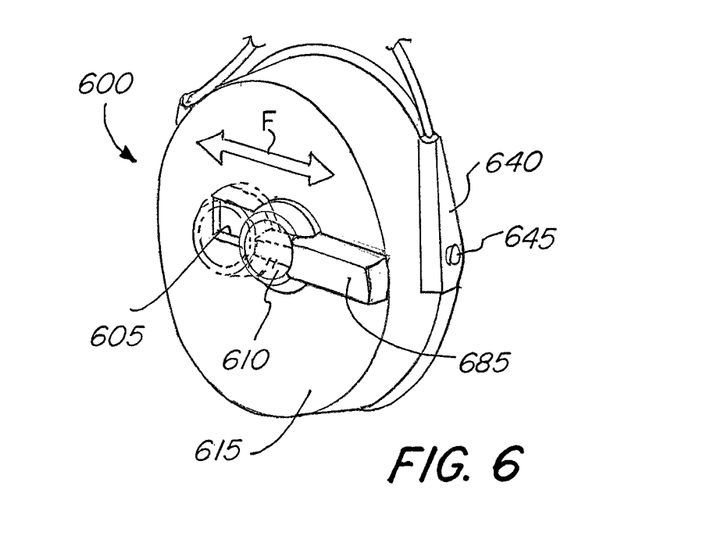
FIG. 6 schematically illustrates a perspective view of a headset having a variable ear attenuator with adjustable attenuation of another embodiment of the invention.

FIG. 6 shows another embodiment of the invention whereby an external power source is used to power the control element. In FIG. 6, attenuator device 600 includes an earcup 615 and a control element 610, the control element 610 able to control the blocking member in the same manner as shown in FIG. 3 and as described in FIGS. 4A-4D.

Additionally, FIG. 6 shows power source 685, the power source 685 being controlled by an external element such as Bluetooth or by a controller.

The power source 685 is able to control amount of sliding of the control element 610, to control attenuation of the device. In certain instances, this is useful as a user may not be able to physically control the control element 610, in the case of a user lacking coordination or even lacking the ability to perform such a maneuver as a result of an injury.

In certain embodiments, the earcup 615 includes a processor and software executing on the processor, such that the software is able to control the power source 685. In certain embodiments, a computer or non-transient medium is used to store instructions to control the power source 685 and the control element.

Referring to FIGS. 7A-7D, another embodiment of the invention is shown. Here, the control element 710 is shown as a knob whereby the knob can be rotated.

Figure 7A:
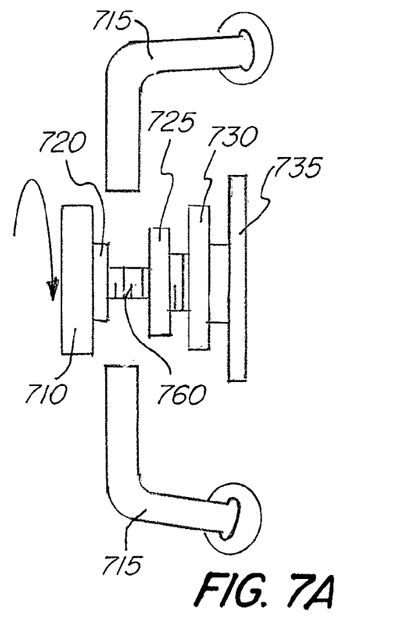
FIGS. 7A-7D schematically illustrate a cross-section view of a headset having a variable ear attenuator with adjustable attenuation of another embodiment of the invention.
Figure 7B:
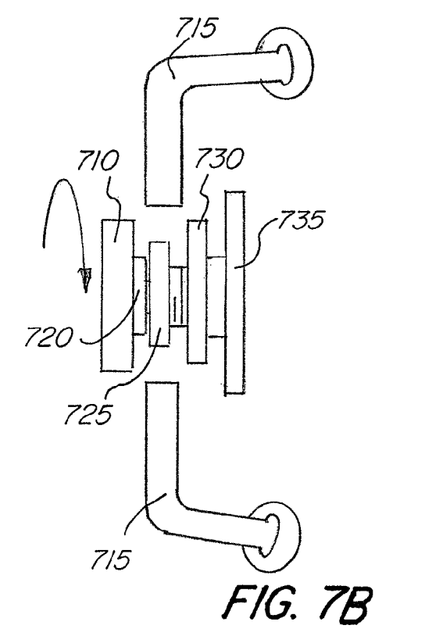
Figure 7C:
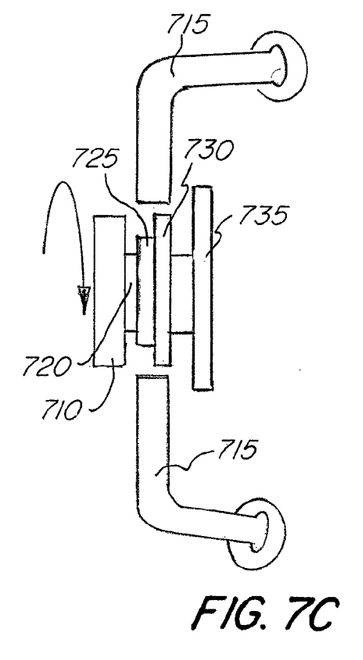
Figure 7D:
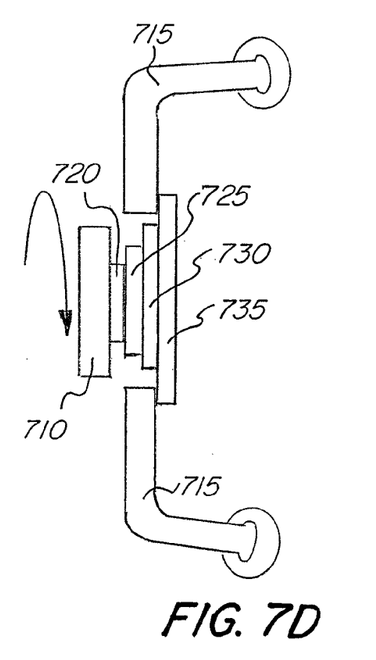

FIG. 7A shows the open position of ear attenuator headset 700. FIG. 7B shows a 60% open position, FIG. 7C shows a 30% open position and FIG. 7D shows a closed position. The control element 710 is rotated to control the amount of attenuation through the at least one earcup 215.

In the cross-section views of FIGS. 7A-7D, the control element 710 is connected via a fastening element 760 (shown as a screw) to various pancake shaped elements 720, 725, 730 and 735. While four pancake shaped elements are shown, either a greater or lesser amount of pancake elements are contemplated as part of the embodiment.

As the control element 710 is rotated, the pancake shaped elements 720, 725, 730 and 735 are drawn into the passageway, thus closing the passageway and obstructing the passageway, thus, providing attenuation. The pancake elements 720, 725, 730 and 735 are blocking members that may be made of attenuating material such as foam, rubber, or other attenuating material.

The pancake elements may be connected via the fastening member 760 or may be connected to one another via a spring or other such element that allows these pancake members to axially move with respect to the control member 710, either towards the control member 710 to close off the passageway, or away from the control member 710 to allow sound to pass through the passageway.

In certain embodiments, the pancake members rotate when the control element 710 is rotated. In other embodiments, the pancake members simply move either towards or away from the control element without rotation of the pancake members.

In certain embodiments of the invention, the control member is controlled by a remote control. In certain embodiments, the remote control allows for a user to close or open the passageway through the at least one earcup allowing for sound to pass through. In certain embodiments, the remote control is located away from or remote from the at least one earcup and in other embodiments, the remote control may be attached to or linked via an electronic cable to the at least one earcup. In certain embodiments, the remote control includes a processor and/or a computer and software executing on a processor to provide control signals to control the amount of attenuation in the earcup.

In certain embodiments, the remote control changes the size of the passageway (also the attenuation space (AS)) based upon the detected amount of sound in the environment. In certain embodiments, the width, length and/or depth of the passageway may be changed by the remote control.

In certain embodiments, the ear attenuator headset includes a sensor or noise detector (such as a microphone) to detect the amount of external sound that is present in the environment. In certain embodiments, the sensor or noise detector is located in the at least one earcup or in the strap. In certain embodiments, the sensor or noise detector is located in the remote control.

In certain embodiments of the invention, variable attenuation is provided in earphones or headphones which deliver sound and in sound monitoring devices, but at the same time also need to provide attenuation, such as in active ear attenuators such as noise cancelling electronic devices. In these embodiments, variable attenuation devices are provided so that external sound can be controlled through the attenuation device.

While the invention has been specifically described in connection with certain specific embodiments thereof, it is to be understood that this is by way of illustration and not of limitation and that various changes and modifications in form and details may be made thereto, and the scope of the appended claims should be construed as broadly as the prior art will permit.

The description of the invention is merely exemplary in nature, and thus, variations that do not depart from the gist of the invention are intended to be within the scope of the invention. Such variations are not to be regarded as a departure from the spirit and scope of the invention.

What is claimed is:

1. An ear attenuator headset comprising:
   at least one earcup, the at least one earcup having a passageway through the at least one earcup allowing for sound to pass through; and
   a control element, the control element able to control the amount of sound that passes through the at least one earcup;
   wherein the control element includes a blocking member, the blocking member configured to move across the passageway to change an amount of sound that passes through the passageway of the at least one earcup;
   wherein when the blocking member is in a closed position the blocking member is aligned with the passageway in the at least one earcup, and when the blocking member is in an open position, the blocking member is not aligned with the passageway in the at least one earcup.

2. The attenuator headset of claim 1, further comprising a headstrap, the head strap connecting a first earcup to a second earcup.

3. The attenuator headset of claim 2, wherein the blocking member slides across the passageway in a straight path to change the amount of sound that passes through the passageway of the at least one earcup.

4. The attenuator headset of claim 3, wherein the at least one earcup includes an audio source.

5. The attenuator headset of claim 4, further comprising a knob connected to the blocking member and having a position indicator.

6. The attenuator headset of claim 3, wherein the blocking member is made of foam attenuating material and/or rubber and/or any other sound blocking material.

7. The attenuator headset of claim 3, wherein the blocking member is connected to a knob.

8. The attenuator headset of claim 1, wherein the blocking member moves along a path transverse to the passageway to control the amount of sound that passes through the passageway.

9. The attenuator headset of claim 1, wherein the at least one earcup includes a plate and wherein when the blocking member is in a closed position, the blocking member engages the plate.

10. The attenuator headset of claim 1, wherein the at least one earcup includes a plate and wherein when the knob is slid to a closed position, the blocking member is aligned with the passageway in the at least one earcup and closes the passageway in the at least one earcup.

11. The attenuator headset of claim 1, wherein the blocking member partially blocks the passageway in the at least one earcup.

12. An ear attenuator headset comprising:
   at least one earcup, the at least one earcup having a passageway through the at least one earcup allowing for sound to pass through; and
   a control element, the control element able to control the amount of sound that passes through the at least one earcup;
   wherein the control element includes a blocking member, the blocking member configured to move across the passageway to change an amount of sound that passes through the passageway of the at least one earcup;
   wherein the control element is controlled by a remote control which closes or opens the passageway through the at least one earcup allowing for sound to pass through;
   wherein the remote control is located remote from the at least one earcup or is attached to or linked via an electronic cable to the at least one earcup and is actuated by a detected amount of sound in the environment.

13. An ear attenuator headset comprising:
   at least one earcup, the at least one earcup having a passageway through the at least one earcup allowing for sound to pass through; and
   a control element, the control element able to control the amount of sound that passes through the at least one earcup;
   wherein the control element is controlled by a remote control which closes or opens the passageway through the at least one earcup allowing for sound to pass through;
   wherein the remote control changes the size of the passageway based upon the detected amount of sound in the environment.

14. The attenuator headset of claim 13, wherein a width, length and/or depth of the passageway is changed by the remote control.

15. The attenuator headset of claim 13, wherein the attenuator headset includes a sensor or noise detector to detect the amount of external sound that is present in the environment.

16. The attenuator headset of claim 13, further comprising a sensor or a noise detector which automatically adjusts an amount of attenuation through the at least one earcup based upon an amount of external sound that is present in the environment.

17. An ear attenuator headset comprising:
   at least one earcup, the at least one earcup having a passageway through the at least one earcup allowing for sound to pass through; and
   a control element, the control element able to control the amount of sound that passes through the at least one earcup;
   wherein the control element includes a blocking member, the blocking member configured to move across the passageway to change an amount of sound that passes through the passageway of the at least one earcup;
   wherein the attenuator headset is able to play music or any sound, while providing control of the amount of sound that passes through the at least one earcup.

18. An ear attenuator headset comprising:
   at least one earcup, the at least one earcup having a passageway through the at least one earcup allowing for sound to pass through;
   a control element, the control element able to control the amount of sound that passes through the at least one earcup; and
   a plurality of attenuator discs, wherein as the control element is adjusted, one of the plurality of discs is inserted into the passageway through the earcup to control the amount sound that passes through the at least one earcup.

19. The attenuator headset of claim 18 wherein as the control element is adjusted to move from an open towards a closed position, the plurality of attenuator discs are progressively inserted into the passageway.

20. The attenuator headset of claim 19, wherein when the knob is rotated, the screw tightens and the blocking member is brought closer to the knob to cover a portion of the passageway.

21. The attenuator headset of claim 18, wherein the blocking member is connected to a knob via a screw.

22. The attenuator headset of claim 18, wherein the control element is controlled by a remote control which closes or opens the passageway through the at least one earcup allowing for sound to pass through.

23. The attenuator headset of claim 22, wherein the remote control is located remote from the at least one earcup or is attached to or linked via an electronic cable to the at least one earcup.

24. The attenuator headset of claim 18 further comprising a sensor or a noise detector which automatically adjusts an amount of attenuation through the at least one earcup based upon an amount of external sound that is present in the environment.

* * * * *